United States Patent
Huang et al.

(10) Patent No.: US 6,293,674 B1
(45) Date of Patent: Sep. 25, 2001

(54) METHOD AND APPARATUS FOR DIAGNOSING AND MONITORING EYE DISEASE

(75) Inventors: David Huang, Cleveland, OH (US); Alan R. Kirschbaum, Oakland; Jay Wei, Fremont, both of CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/614,537

(22) Filed: Jul. 11, 2000

(51) Int. Cl.$^7$ .................................................... A61B 3/10
(52) U.S. Cl. ............................................................ 351/221
(58) Field of Search ................................... 351/208, 209, 351/210, 214, 221, 205; 382/103, 131

(56) References Cited

U.S. PATENT DOCUMENTS

| | | | |
|---|---|---|---|
| 5,321,501 | 6/1994 | Swanson et al. | 356/345 |
| 5,459,570 | 10/1995 | Swanson et al. | 356/345 |
| 5,644,642 | * 7/1997 | Kirschbaum | 382/103 |

OTHER PUBLICATIONS

"Optical Coherence Tomography" by Huang et al., *Science*, vol. 254, pp. 1178–1181, Nov. 22, 1991.

"In vivo retinal imaging by optical coherence tomography" by Swanson et al., *Optics Letters*, vol. 18, No. 21, pp. 1864–1866, Nov. 1, 1993.

Micrometer–Scale Resoution Imaging of the Anterior Eye In Vivo With Optical Coherence Tomography, by Izatt et al., *Arch. Ophthalmol.*, vol. 112, pp. 1584–1589, 1994.

"Optical Coherence Tomography of the Human Retina" by Hee et al., *Arch. Ophthalmol.*, vol. 113, pp. 325–332, 1995.

"Imaging of Macular Diseases with Optical Coherence Tomography" by Puliafito et al., *Ophthalmology*, vol. 102, pp. 217–229, 1995.

"Optical Coherence Tomography of Macular Holes" by Hee et al., *Ophthalmology*, vol. 102, pp. 748–755, 1995.

"Quantification of Nerve Fiber Layer Thickness in Normal and Glaucomatous Eyes Using Optical Coherence Tomography" by Schman et al., *Arch. Ophthalmol.*, vol. 113, pp. 586–596, 1995.

"Reproducibility of Nerve Fiber Layer Thickness Measurements Using Optical Coherence Tomography " by Schuman et al., *Ophthalmology*, vol. 103, pp. 1889–1898, 1996.

"A New Algorithm for Retinal Nerve Fiber Layer Thickness Measurement by Optical Coherence Tomography" by Huang et al., *Inv. Opthal and Vis. Sci.*, vol. 37, No. 3, Feb. 15, 1996.

"Retinal Nerve Fiber Layer Distribution as Measured by Optical Coherence Tomography" by Nguyen et al., *Inv. Opthal and Vis. Sci.*, vol. 37, No. 3, Feb. 15, 1996.

"Assesment of Retinal Nerve Fiber Layer (RNFL) Internal Reflectivity Using Optical Coherence Tomography (OCT)" by Pons et al., *Inv. Opthal and Vis. Sci.*, vol. 40, No. 4, Mar. 15, 1999.

* cited by examiner

*Primary Examiner*—George Manuel
(74) *Attorney, Agent, or Firm*—Michael B. Einschlag (57) ABSTRACT

Embodiments of the present invention provide method and apparatus for diagnosing and monitoring eye disease such as, for example, glaucoma. In particular, embodiments of the present invention analyze OCT scans of a retina to determine one or more of the following measures for diagnosing and monitoring glaucomatous retinal nerve fiber layer ("NFL") change: an NFL thickness; a ratio of NFL thickness in a vertical quadrant (superior and inferior quadrants in an OCT scan are combined in a vertical average) and a horizontal quadrant (nasal and temporal quadrants in the OCT scan are combined in a horizontal average); and an NFL signal ratio ("NSR") of a sum of signal strengths in a predetermined portion of the NFL and a sum of signal strengths in a predetermined region below a retina-pigment epithelium ("RPE") interface.

20 Claims, 4 Drawing Sheets

METHOD AND APPARATUS FOR DIAGNOSING AND MONITORING EYE DISEASE

TECHNICAL FIELD OF THE INVENTION

The present invention pertains to method and apparatus for diagnosing and monitoring eye disease such as, for example, glaucoma. In particular, the present invention pertains to method and apparatus for diagnosing and monitoring eye disease by determining measures that are sensitive to eye disease.

BACKGROUND OF THE INVENTION

As is well known, glaucoma produces a progressive loss (usually in a slow, characteristic fashion) of the retinal nerve fiber layer ("NFL") that is related to elevated intraocular pressure and other possible causative factors. The loss of NFL due to glaucoma leads to constriction of visual field, and may end in blindness. Up to now, there has been no reliable and sensitive method of diagnosing and monitoring glaucomatous damage to the NFL, or to visual function. Current clinical diagnosis of glaucoma relies on clinical history, intraocular pressure measurements, optic disc and NFL biomicroscopy and photography, and visual field testing. None of these methods alone has good sensitivity and specificity in the detection of glaucoma or glaucoma progression. However, taken together, they constitute a current diagnostic standard due to lack of better methods. Development of other techniques such as automated optic disc analysis by scanning laser ophthalmoscopy, and NFL assessment by scanning laser polarimetry has improved the reproducibility of measurements, but still has not demonstrated reliable and sensitive detection of glaucomatous damage.

Optical coherence tomography ("OCT") is a noninvasive technology that can produce cross-sectional images of tissues with ten (10) micron axial resolution. For example, see an article by D. Huang et al. entitled "Optical Coherence Tomography," *Science,* vol. 284, 1991, pp. 1178–1181. In particular, OCT can be used to image tissues within the human eye. For example, OCT systems suitable for non-contact imaging of vitreo-retino-choroidal structures are known in the art.

In OCT images, the NFL can be distinguished from other structures by its high reflected signal amplitude, see an article by Hee et al. entitled "Optical Coherence Tomography of the Human Retina," *Archive of Ophthalmology,* vol. 113, 1995, pp. 325–332 ("Hee et al."). Implementation of OCT for general tissue imaging, and for eye imaging, is disclosed in U.S. Pat. No. 5,321,501 to Swanson et al. In OCT imaging, a probe beam is focused on an eye structure of interest, and resulting optical reflections are analyzed in a low coherence interferometer. The interferometer resolves the signals reflected at various tissue depths by their optical delays. Lateral scanning of the probe beam provides information in a transverse dimension. The data can then be displayed as a tomograph, or cross-sectional image, of the tissue's reflected signal strength.

Computerized analysis of OCT images can yield quantitative information on the status of the NFL, and can have utility in the diagnosis and management of glaucoma and other optic neuropathies.

In investigating the retina, it is advantageous to scan an OCT beam in a predetermined path transversely across the retina, while at the same time, performing axial (depth) scans at multiple locations along the transverse scan path. For the purpose of measuring NFL, the scan path, as described in Hee et al., is a circle centered on the optic nerve head. By displaying all the axial scans together using a false-color or grayscale display, it is possible to create a two-dimensional "slice" of the tissue in which a vertical axis corresponds to depth in the tissue, and a horizontal axis corresponds to lateral position of the scan beam. A typical axial scan will show: (a) a high signal peak corresponding to inner retinal structures, i.e., the vitreo-retinal interface ("VRI") and the NFL layer; (b) a region of varied intermediate signals corresponding to the nuclear and plexiform layers; (c) a region of low signal corresponding to the photoreceptor layer ("PRL"); and (d) another region of high signal corresponding to the outer retinal and inner choroidal structures, i.e., the retina-pigment epithelium ("RPE") and the choriocapillaris.

One prior art method has been developed that detects the NFL based solely on relative reflectivity, see an article by Schuman et al. entitled "Reproducibility of Nerve Fiber Layer Thickness Measurements Using Optical Coherence Tomography," *Ophthalmology,* vol. 103, 1996, pp. 1889–1898 ("Schuman et al."). As described in Schuman et al., an image processing computer program determined total retinal thickness and retinal nerve fiber layer thickness for cylindrical OCT sections obtained by scanning around the optic nerve head (because axial information was obtained with OCT, circular scans produced a cylinder in three (3) dimensions). The images were corrected for artifacts due to involuntary subject motion during data acquisition using a standard image processing technique of cross-section scan registration. After subject motion in the longitudinal direction was corrected with a cross-correlation scan registration technique, a digital filter was applied to smooth the tomograms and reduce image speckle noise. Two-dimensional linear convolution with a center-weighted kernel was used to reduce speckle variations. Retinal thickness was quantitated by computer for each axial scan in the image as the distance between the first reflections at the vitreo-retinal interface and the anterior boundary of the reflective layer corresponding to the retinal pigment epithelium and choriocapillaris. Nerve fiber layer thickness was determined by computer. Boundaries were located by searching for the first points on each scan where the reflectivities exceeded a certain threshold. For example, an inner limiting membrane was located by starting anteriorly and searching downward in the image. A posterior margin of the nerve fiber layer was located by starting within the photoreceptor layer and searching upward in the image. The location of the photoreceptor layer was assumed to lie at the position of minimum reflectivity within the neurosensory retina. Thresholds were separately determined by the computer for each scan in the image as a fixed decibel level below the maximum signal in the scan.

Note that the above-described prior art method identifies NFL boundaries solely on the basis of a fixed relative signal strength regardless of where the maximum signal occurs, and does not take into account the fact that the signal from the outer retina is determined in part by how much light is reflected from the inner retina. Since NFL thickness is correlated with NFL signal strength, scans of tissue having minimal NFL will have too high a threshold, resulting in anomalously low thicknesses. In addition, attempting to locate an NFL boundary based on this threshold is subject to error, since signal fluctuation near the threshold value can lead to significant variation in the boundary.

As one can readily appreciate from the above, a need exists in the art for method and apparatus for diagnosing and monitoring eye disease such as, for example, glaucoma.

SUMMARY OF THE INVENTION

Embodiments of the present invention advantageously satisfy the above-identified need in the art and provide method and apparatus for diagnosing and monitoring eye disease such as, for example, glaucoma. In particular, embodiments of the present invention provide method and apparatus for diagnosing and monitoring eye disease by determining measures that are sensitive to eye disease.

In particular, embodiments of the present invention analyze OCT scans of a retina to determine one or more of the following measures for diagnosing and monitoring glaucomatous retinal nerve fiber layer ("NFL") change: an NFL thickness; a ratio of NFL thickness in a vertical quadrant (superior and inferior quadrants in an OCT scan are combined in a vertical average) and a horizontal quadrant (nasal and temporal quadrants in the OCT scan are combined in a horizontal average); and an NFL signal ratio ("NSR") of a sum of signal strengths in a predetermined portion of the NFL and a sum of signal strengths in a predetermined region below a retina-pigment epithelium ("RPE") interface.

Specifically, a first embodiment of the present invention is a method for providing a measure for diagnosing and monitoring eye disease which comprises the steps of: (a) OCT scanning a retina of an eye to obtain an OCT scan image; (b) aligning axial scans in the OCT scan image; (c) for each axial scan in the OCT scan image: (i) locating a vitreo-retinal interface ("VRI") and a retina-pigment epithelium ("RPE") interface; (ii) determining a threshold as a function of signal statistics in the axial scan; and (iii) determining a thickness of the NFL by counting pixels between the VRI and RPE interfaces that exceed the threshold; and (d) averaging the thickness of the NFL over predetermined axial scans to provide the one or more measures.

A second embodiment of the present invention is a method for providing a measure for diagnosing and monitoring eye disease which comprises the steps of: (a) OCT scanning a retina of an eye to obtain an OCT scan image; (b) aligning axial scans in the OCT scan image; (c) for each axial scan in the OCT scan image: (i) locating a vitreo-retinal interface ("VRI") and a retina-pigment epithelium ("RPE") interface; (ii) for a predetermined portion of the axial scan below the RPE interface ("reference window"), summing the signal strengths; and (iii) for a predetermined portion of the axial scan below the VRI interface ("NFL window"), summing the signal strengths; (d) averaging a representation of the sum of signal strengths in the reference window over predetermined axial scans; (e) averaging a representation of the sum of signals strengths in the NFL window over predetermined axial scans; and (f) determining a ratio of the averages to form the measure.

DETAILED DESCRIPTION

Figure 1:
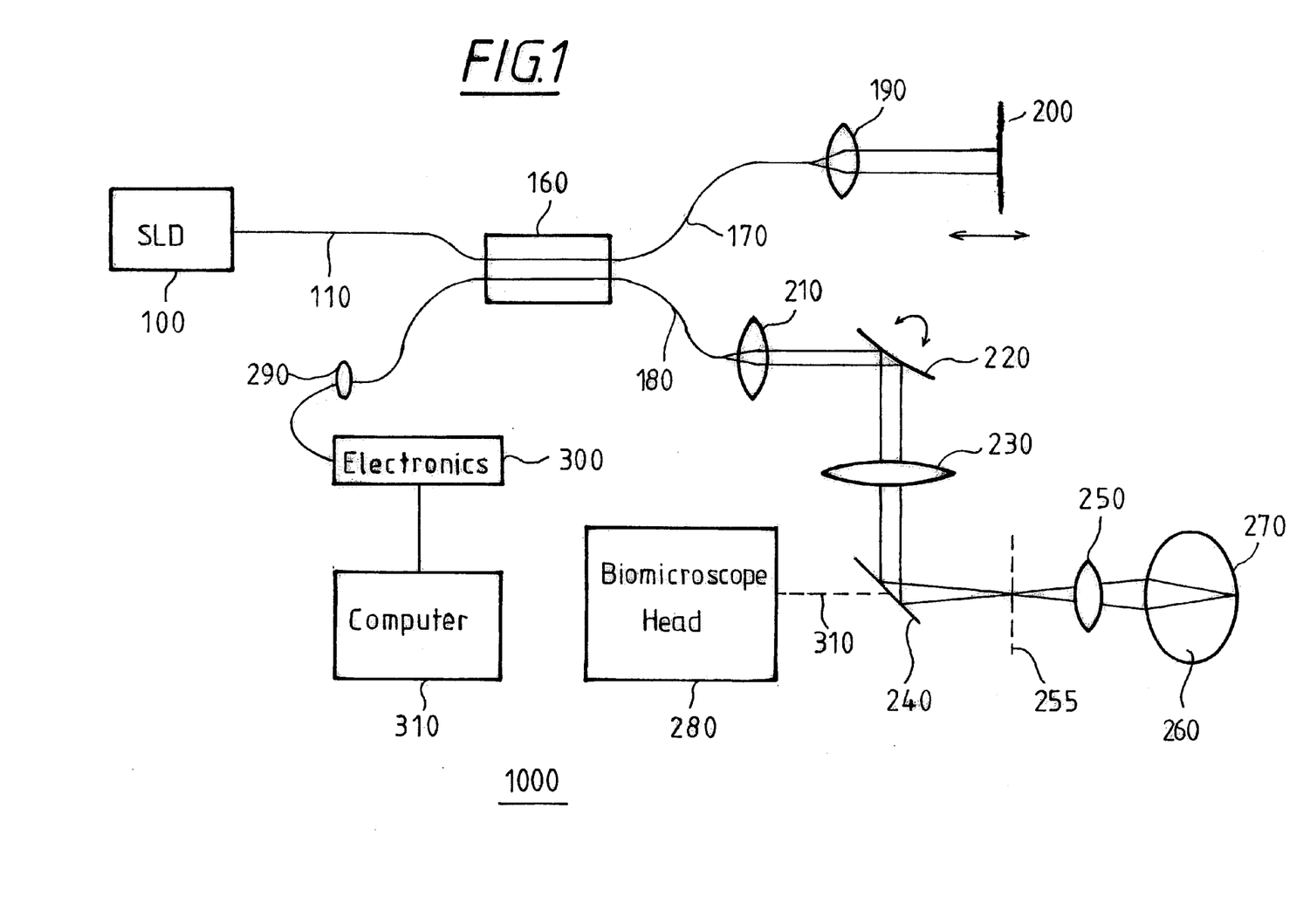
FIG. 1 shows a block diagram of an optical coherence tomography ("OCT") apparatus used to fabricate embodiments of the present invention.

FIG. 1 shows optical coherence tomography ("OCT") apparatus 1000 used to fabricate an embodiment of the present invention. However, it should be understood that the present invention is not limited by the type of OCT apparatus used to obtain OCT data. As such, any one of a number of OCT apparatus which are well known to those of ordinary skill in the art may be used to fabricate embodiments of the present invention.

As shown in FIG. 1, OCT apparatus 1000 comprises a fiber optic delivery system that couples a low coherence reflectometer to a biomicroscope. In particular, as shown in FIG. 1, a beam of radiation output from superluminescent diode ("SLD") 100 has a wavelength centered substantially at about 843 nm wavelength, and is applied as input to optical fiber 110. In accordance with both preferred embodiments of the present invention, all optical fibers are single mode optical fibers. Radiation output from optical fiber 110 is applied as input to coupler 160, and coupler 160 in turn, applies a first portion (typically about 50%) of the input radiation as input to optical fiber 170 and a second portion (typically about 50%) of the input radiation as input optical fiber 180. As further shown in FIG. 1, radiation output from optical fiber 170 passes through collimating lens 190, and impinges on moving reference mirror 200. It should be understood that reference mirror may also be implemented using a corner cube, or using any one of a number of reflectance mechanisms that are available in the art for fabricating OCT apparatus. Mirror 200 is moved, for example, at a constant velocity, in accordance with any one of a number of apparatus (not shown) that are well known to those of ordinary skill in the art. Radiation reflected from reference mirror 200 passes through collimating lens 190, is applied as input to optical fiber 170, and, is applied, in turn, as input to coupler 160.

Radiation output from optical fiber 180 passes through collimating lens 210, and impinges on transverse scanning mirrors 220, which transverse scanning mirrors 220 are controlled in accordance with methods that are well known in the art to scan an OCT probe beam. Radiation output from transverse scanning mirrors 220 passes through focusing lens 230, and impinges upon beamsplitter 240. The beam focus is coincident with biomicroscope image plane 255. This allows visualization of the fundus with a CCD camera while OCT scanning is performed.

Radiation reflected by beamsplitter 240 passes through condensing lens 250 (for example, a 78 Diopter Volk lens, Volk, Inc. of Mentor Ohio), and impinges upon retina 270 of eye 260. Focusing lens 230 and condensing lens 250 are designed to image the scanning pupil (i.e., the face of transverse scanning mirrors 220) onto the entrance pupil of eye 260 to minimize vignetting. Radiation reflected from retina 270 passes back through eye 260, condensing lens 250, and impinges upon beamsplitter 240. A portion of the reflected radiation passes through beamsplitter 240, and impinges upon biomicroscope head 280. Another portion of the reflected radiation is reflected by beamsplitter 240 and passes back through focusing lens 230, transverse scanning mirrors 220, collimating lens 210, optical fiber 180 and, is applied, in turn, as input to coupler 160.

Radiation reflected from reference mirror 200 interacts with radiation reflected from retina 270 in a manner that is well known to those of ordinary skill in the art to produce OCT output radiation, which OCT output radiation is applied as input to photodetector 290. Output from photodetector 290 is applied as input to electronics 300 (for example, a bandpass filter, which bandpass filter is followed by an envelope detector, which envelope detector is followed, in turn, by an analog-to-digital detector). Lastly, the output from electronics 300 is applied as input to computer 310.

The retinal examination performed using OCT apparatus 1000 is carried out in a manner similar to a retinal examination performed using slit-lamp ophthalmoscopy, with the restriction that condensing lens 250 is mounted and fixed along optical axis 310 of biomicroscope head 280. After eye 260 is dilated, and the patient is positioned comfortably in a headrest (not shown) of biomicroscope head 280, biomicroscope head 280 and condensing lens 250 are positioned along the optical axis of eye 260. The entire unit is brought forward until an image of transverse scanning mirrors 220 is placed onto the pupil plane of eye 260. The position of condensing lens 250 is then adjusted along optical axis 310, relative to biomicroscope head 280, until the image of the fundus is brought into focus. This adjustment compensates for differences in refractive power between subject eyes without being affected by accommodation in the examiner's eye.

An infrared-sensitive charge coupled device ("CCD") video camera (not shown) attached to biomicroscope head 280 provides a video image of the scanning OCT probe beam on the fundus, and permits the position of each tomograph on the retina to be documented.

A desired scanning position is then located while the examiner observes both a real time display of the OCT progress, and the video image of the OCT probe beam located on the fundus. The OCT examination can also be performed on an undilated or poorly dilated pupil; however, the optical alignment is more sensitive to aperturing by the pupil, and the field of view is reduced.

As is well known, resolution of the axial position of backscattered radiation from eye 260 is provided by scanning the position of reference mirror 200. In an OCT system used to make measurements, assuming a tissue refractive index of 1.36, the axial resolution in the tissue is roughly ten (10) microns full-width half-maximum. In accordance with one embodiment of the present invention, analog output from photodetector 290 is digitized at a rate that produces an axial pixel size of about 4.0 microns. According to the Nyquist criterion for digital sampling, the axial pixel size is preferentially roughly one-half, or less, of the axial resolution of the low coherence reflectometer. As is well known, lateral resolution is limited by the image acquisition time, and is given by the total lateral scan range divided by the number of axial scans. In accordance with this embodiment of the present invention, OCT apparatus 1000 makes one-hundred (100) axial scans per image. Future OCT units are likely to oversample (and produce an axial pixel size of less than 4 microns) and acquire more axial scans over shorter period of time.

Retinal nerve fiber layer ("NFL") loss is the anatomic bottom line in both glaucoma and other types of optic neuropathies. Embodiments of the present invention provide measures useful for assessing the NFL to diagnosis and monitor these disease processes.

In accordance with embodiments of the present invention, algorithms are provided to analyze data obtained from OCT scans of the retina and choroid of eye 260 in a region around the optic disc (also called the optic nerve head or the papilla) to determine measures used to diagnose and monitor eye disease. Further, in accordance with other embodiments of the present invention, such measures are stored. Many methods and apparatus are well known to those of ordinary skill in the art for storing such measures in databases that can store and retrieve the data relating to specific patients. Examples of such databases and apparatus are databases stored on disk storage that are accessible from a computer such as, for example, a personal computer. Still further, in accordance with these other embodiments of the present invention, the measures are compared with measures taken from normal eyes to diagnose eye disease, and the measures may also be compared with measures taken from the same patients (made over a period of time) to enable monitoring of eye disease.

Figure 2:
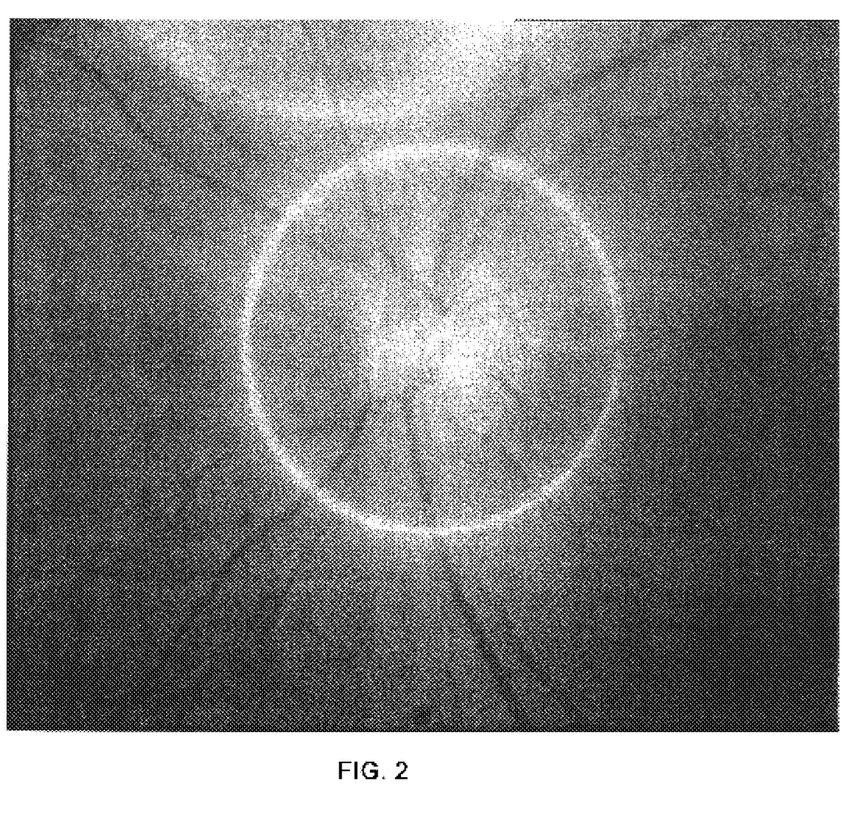
FIG. 2 shows an image of an optic disc and its surrounding structures in a human eye, and a circular scan around the optic disc in accordance with one embodiment of the present invention.

FIG. 2 shows an image of an optic disc and its surrounding structures in a human right eye. The optic disc is the central structure in FIG. 2. Retinal blood vessels emanate from the center of the optic disc. Above the optic disc lies the superior retina, below the optic disc lies the inferior retina, to the left of the optic disc lies the temporal retina, and to the right of the optic disc lies the nasal retina. The terms temporal and nasal refer to directions toward structures of the head (the temple), and the nose, respectively. The arrangement of structures in a left eye is a mirror image of that in the right. Clockhour designations are assigned for the right eye by imposing a conceptual clockface on retinal structures in the orientation shown in FIG. 2. A mirror clockface is also applied to the structures in the left eye so that 9 o'clock always refers to the temporal direction, and 3 o'clock the nasal direction.

As further shown in FIG. 2, the optic disc is where the optic nerve exits the eye, and has typical diameters of 1.75 mm vertically and 1.5 mm horizontally. However, the optic disc diameter varies by a factor of 2–3 among the normal human population. In accordance with a preferred embodiment of the present invention, an OCT scan is preferably circular, and centered on the scleral margin of the optic disc. In FIG. 2, a 3.37 mm diameter scanning path of the OCT probe beam is traced out by the white circular line. The diameter of the OCT scan is preferably large enough to include the great majority of optic disc sizes. However, the scan diameter should not be too large because the NFL becomes thinner with greater distance form the disc. A diameter of 3.37 mm, or roughly two (2) times the average disc diameter, is considered to be a reasonable compromise. However, the present invention is not limited thereto, and the scan can have other diameters and, in fact, need not be circular.

In practice, an axial scan obtained with OCT apparatus 1000 had 500 axial elements. However, to better show details of chorioretinal structures, images were cropped axially. The horizontal or lateral dimension in an image represents locations along the circular scan, and the vertical dimension in the image represents locations along the axial scan. The pixel dimensions were 3.6 degrees laterally, and 4.0. microns axially.

Figure 3:
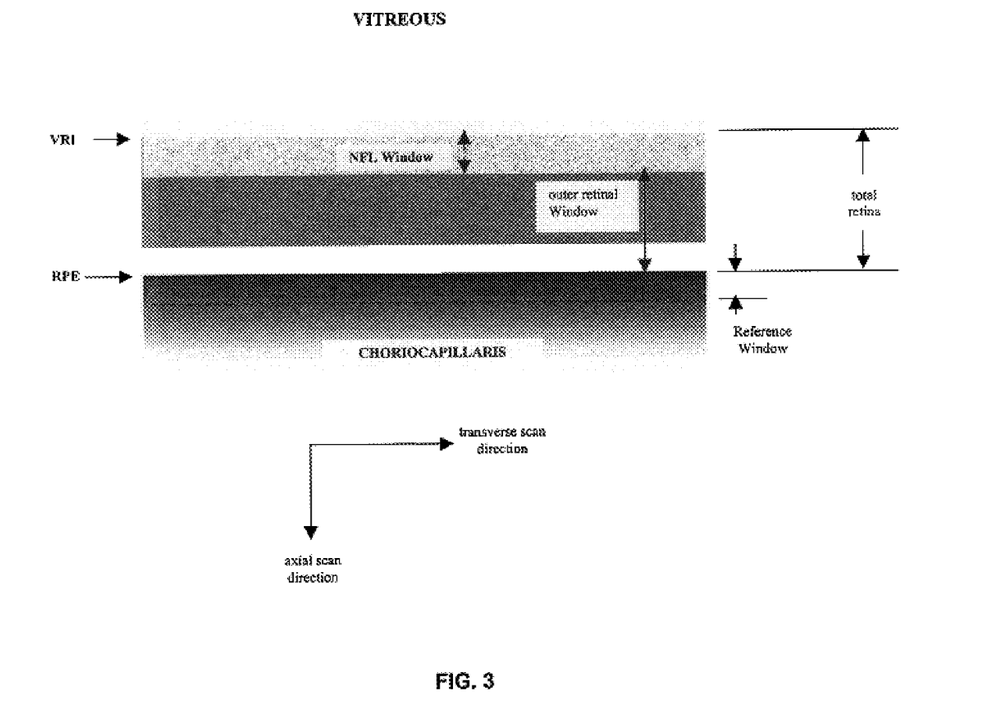
FIG. 3 schematically shows part of a cylindrical cross-section of tissue surrounding an optic nerve head; OCT axial scans are made at discrete locations along this cross-section.

An OCT axial scan of peripapillary chorioretinal structures results in recognizable structures: NFL (highest signal level); plexiform and nuclear layers (intermediate variable signal level); photoreceptors (low signal level); RPE and choriocapillaris (high signal level), and outer choroid and sclera (gradually decreasing signal level). FIG. 3 schematically shows part of a cylindrical cross-section of tissue surrounding an optic nerve head; axial scans are made at discrete locations along this cross-section. FIG. 3 shows the relative locations (from top to bottom) of: (a) the vitreous; (b) the vitreo-retinal interface ("VRI"); (c) the NFL; (d) the photoreceptor layer ("PRL"); (e) the retina-pigment epithelium ("RPE"); and (f) the choriocapillaris.

Algorithm to Determine a Measure for a First Embodiment of the Present Invention The following describes an algorithm fabricated in accordance with a first embodiment of the present invention that determines measures that are useful for diagnosing and monitoring glaucoma. These measure are an NFL thickness and a ratio of NFL thickness in a vertical quadrant (superior and inferior quadrants in an OCT scan are combined in a vertical average) and a horizontal quadrant (nasal and temporal quadrants in the OCT scan are combined in a horizontal average).

The first step of the algorithm of the first embodiment of the present invention is to convert the data to decibel (dB) form. Because tissue structures of the choroid have wide-ranging backscattering properties, it is advantageous to convert OCT raw data to a logarithmic scale to reveal details of more weakly backscattering structures. This is true for visual inspection of OCT images, and/or for subsequent digital processing. In order for digital processing to distinguish tissues optimally, it is desirable to use a method whereby a particular retinal or choroidal layer is consistently assigned similar signal values (Note that it is not possible to achieve this goal perfectly because many uncontrolled factors influence the absolute OCT-to-tissue optical coupling, and the relative contrast between tissue layers). However, in accordance with the first embodiment of the present invention, a logarithmic scale is based on a signal standard deviation measured in a vitreous region of the OCT image. Advantageously, this substantially measures background optical shot noise of OCT apparatus 1000 because no significant backscattering is expected from the normal vitreous media in the eye, which normal vitreous media is highly transparent. In accordance with one version of the first embodiment of the present invention, a second row from a top of an OCT image is used to calculate the standard deviation. This is done to avoid possible noise in a first row due to imperfect initiation of an analog-to-digital conversion cycle. Alternatively, other regions of the image, or known calibration values, can be used to establish the background noise of OCT apparatus 1000. In accordance with the first embodiment of the present invention, the background noise standard deviation is defined as 0 dB, and a signal level ten (10) times that of the noise standard deviation is defined as 20 dB. This assumes that an analog signal output from OCT apparatus 1000 is linear with a photodetector signal output from the interferometer portion of OCT apparatus 1000. If an analog logarithmic amplifier, or other electrical means, is used to modify the OCT signal, then the digital processing can be modified to code the OCT data in a similar dB-scale. Note that the dB-scale can be based on other alternative reference signal levels such as the maximum signal amplitude in the image, or in each axial scan.

The next step of the algorithm of the first embodiment of the present invention is to align the axial scans. During acquisition of the OCT image, an operator should adjust the axial scan range so that the retina and choroid are included in the image. However, the location of each retinal and choroidal tissue layer in the image is not known. Further, the location of tissue layers can vary between axial scans comprising the OCT image due to: (a) tilt of the OCT probe beam relative to the plane of the peripapillary retina; (b) anatomic variations in tissue location; and (c) movement of the eye during the image acquisition period. Axial alignment of tissue layers in each axial scan is performed so they appear at substantially the same axial depths. In accordance with the first embodiment of the present invention, alignment of the axial scans is done by cross-correlating axial scans with a reference scan waveform to determine their relative shift; cross-correlation is an image processing method which is well known to those of ordinary skill in the art. Once the relative shifts are determined, the axial scans are shifted to bring the corresponding anatomical features into registration. In the first embodiment, the center of the PRL is shifted to pixel number 100 and the axial scan is cropped outside of pixels 0 to 199.

Optionally, a next step of the first embodiment of the present invention is to reorganize the OCT image, left-to-right, in the order of superior-nasal-inferior-temporal. This data organization is arbitrary, and other conventions can be adopted as long as they are used consistently.

Optionally, a next step of the first embodiment of the present invention is to smooth the data. This is done, for example, using convolution with a two-dimensional, center-weighted kernel.

The next step of the first embodiment of the present invention is to determine a threshold for use in locating the VRI and RPE interfaces. In accordance with the first embodiment of the present, for each axial scan, the signal level of the brightest pixel in the retinal region is obtained ("maximum retinal signal"). Lateral low-pass filtering of the maximum retinal signal is performed by local averaging over, for example and without limitation, eleven (11) neighboring axial scans to reduce the influence of spurious variation in signal levels. After local averaging, the threshold is set equal to for example and without limitation, 15 dB below the maximum retinal signal.

The next step of the first embodiment of the present invention is to locate the VRI interface for each axial scan by searching, for example and without limitation, from pixel 0 downward until the first pixel with a suprathreshold signal is found. The threshold is determined to be, for example and without limitation, 14 dB below the maximum retinal signal.

The next step of the first embodiment of the present invention is to locate the RPE interface for each axial scan by searching from an approximate location of the PRL (for example and without limitation, from pixel 101) downward until the first suprathreshold pixel is found. The threshold is determined to be, for example and without limitation, 7 dB below the maximum retinal signal for all pixels lying below the PRL.

Before describing further steps, refer to FIG. 3 to understand some nomenclature. As shown in FIG. 3, a reference window is defined for each axial scan to extend from the RPE interface to a fixed distance below the RPE interface, which reference window includes a segment of largest signal strength within the RPE-choriocapillaris signal complex. In accordance with one embodiment of the present invention, the fixed distance chosen, for example and without limitation, to be 58 $\mu$m.

The next step of the first embodiment of the present invention is to sum signal values from each axial scan within the reference window; these sums will be referred to below as reference signal sums.

The next step of the first embodiment of the present invention is to take into account shadowing by blood vessels. There are numerous branches of retinal arteries and veins that cross the OCT probe beam path. These blood vessels are known to lie in the inner (top) portion of the NFL. Because the larger blood vessels produce clear shadowing of the choriocapillaris, they also shadow the NFL underneath them. Thus, NFL measurement at the positions of the major blood vessels may not be reliable. In accordance with the first embodiment of the present invention, the position of these blood vessels is detected by comparing the reference signal sum for each axial scan against those for a predetermined number of neighboring axial scans centered on the axial scan of interest. If the reference signal sum is a predetermined amount, for example and without limitation, 7.5 dB or more, below that of the local average, this axial scan is, for example and without limitation, eliminated or it is replaced by local or global averages. This replacement occurs without much change in the result because a combined width of the four (4) major retinal branch vessels exiting the optic disc is roughly six hundred (600) microns (see "Atlas of Fluorescein Angiography" by A. E. Jalkh and J. M. Celorio, W. B. Saunders, Philadelphia, 1993, p. 19; and thus occupies roughly six percent (6%) of an OCT scan circumference, given a 3.37 mm scan diameter).

The next step of the first embodiment of the present invention is to determine a threshold for use in computing the NFL thickness for each axial scan. One should readily appreciate that the threshold may vary from axial scan to axial scan due to changes in optical coupling and the polarization state of the OCT probe beam. To determine the threshold for each axial scan, the maximum retinal signal and the reference signal sum are lateral, low-pass filtered by local averaging over, for example and without limitation, eleven (11) neighboring axial scans to reduce the influence of spurious variation in signal levels. After local averaging, the reference signal sum is averaged over the reference window. Then, the maximum retinal signal and the average reference signal sum are converted from the dB-scale to a scale linear with optical intensity. The linear scale signals are then summed and converted back to the dB scale. The threshold is set, for example and without limitation, at 8 dB below the sum. It is believed that the use of the average reference signal sum in the calculation of the threshold will reduce excessive lowering of the threshold in glaucomatous eyes.

The next step of the first embodiment of the present invention is to compute the NFL thickness for each axial scan by counting the number of pixels above the threshold value between the VRI and the RPE.

The next step of the first embodiment of the present invention is to average the NFL thickness: (a) over each quadrant region; and (b) over the entire circular scan. Then, the superior and inferior quadrants are combined in a vertical average and the nasal and temporal quadrants are combined in a horizontal average. It is believed that the ratio of the vertical average over the horizontal average has a special relevance to glaucoma where nerve fiber loss generally occurs earlier, and is more severe in the vertical quadrants.

Overall, tests with subjects showed that the following measures are useful for diagnosing and monitoring glaucomatous NFL change: NFL thickness, and the vertical/horizontal NFL thickness ratio.

Algorithm to Determine a Measure for a Second Embodiment of the Present Invention The following describes an algorithm fabricated in accordance with a second embodiment of the present invention that defines a further measure that is useful for diagnosing and monitoring glaucomatous change. This further measure, referred to below as an NFL signal ratio (NSR), is based on signal reflectance ratios. In determining NSR, NFL thickness is not directly measured, and no threshold computation is needed for detection of the outer NFL boundary.

The first step of the algorithm of the second embodiment of the present invention is to convert the data to decibel (dB) form using the same method described in detail above for the first embodiment.

The next step of the algorithm of the second embodiment of the present invention is to align the axial scans. In accordance with the second embodiment of the present invention, alignment of the axial scans is done by cross-correlating adjacent axial scans to determine their relative shift; cross-correlation is an image processing method which is well known to those of ordinary skill in the art. Once the relative shifts are determined, the axial scans are shifted to bring the corresponding anatomical features into registration.

Optionally, a next step of the second embodiment of the present invention is to smooth the data. This may be done using the same method as that described in detail above for the first embodiment.

The next step of the second embodiment of the present invention is to locate the VRI and RPE interfaces. Since these interfaces are characterized by strong and abruptly changing signal strength, their determination is generally unambiguous and relatively independent of algorithm parameters. In accordance with the second embodiment of the present invention, these interfaces are detected using edge-detection methods such as, for example and without limitation, a one-dimensional convolution of each axial scan using an appropriate edge-detecting kernel to afford an accurate measure of its location.

Before describing further steps, refer to FIG. 3 to understand some nomenclature. As shown in FIG. 3, a reference window is defined for each axial scan to extend from the RPE interface to a fixed distance below the RPE interface, which reference window includes a segment of largest signal strength within the RPE-choriocapillaris signal complex. In accordance with one version of the second embodiment of the present invention, the fixed distance is chosen, for example and without limitation, to be 58 $\mu$m.

The next step (referring to FIG. 3) of the second embodiment of the present invention is to sum signal values from each axial scan within the reference window. It has been found advantageous to do this summation in the linear signal domain rather than the logarithmic (dB) domain. Thus, for the $i^{th}$ axial scan, there will be a corresponding sum denoted as $S_{Ref}(i)$.

The next step of the second embodiment of the present invention is to examine $S_{Ref}(i)$ to determine whether the signal is "abnormally" reduced due to "shadowing" by overlying blood vessels in the retinal layers. In accordance with the second embodiment of the present invention, a shadow is deemed to occur at the $i^{th}$ axial scan if the ratio of $S_{Ref}(i)$ to a local average of $S_{Ref}$ over a predetermined number of axial scans surrounding i is less than a predetermined dB value. The values of i for which shadowing occurs are saved for later use.

The next step (referring to FIG. 3) of the second embodiment of the present invention is, for each axial scan, to subdivide the total retinal thickness (i.e., the distance between the VRI and RPE interfaces) into an "NFL Window" and an "Outer Retinal Window." In accordance with the second embodiment of the present invention, the Outer Retinal Window is chosen to begin at the RPE and extend upward (on the image, i.e., inward into the eye), for example and without limitation, for 142 microns. The distance of 142 microns was based on a difference between an average retinal thickness and an average NFL thickness as measured in a sample of normal eyes. The NFL Window is taken as the remaining inner retina above (on the image) the Outer Retinal Window. Note that, because total retinal thickness varies by axial scan, the width of the NFL Window varies accordingly. Then, within the NFL Window, the signal values from each axial scan are summed (also in the linear intensity domain). Thus, for the $i^{th}$ axial scan, there will be a corresponding sum denoted as $S_{nfl}(i)$. Although the NFL Window corresponds to the average location of NFL, exact anatomic correspondence in each case is neither expected nor required.

The next step of the second embodiment of the present invention, if shadowing occurs at the $i^{th}$ axial scan, is to replace the values of $S_{nfl}(i)$ and $S_{Ref}(i)$ with values interpolated using values bordering the shadowed region.

The next step of the second embodiment of the present invention is to group the axial scans which are acquired along, for example and without limitation, a circular locus, into quadrants. All signal sums $S_{Ref}$ and $S_{nfl}$ arising from axial scans within the $j^{th}$ quadrant are averaged together:

$$A(j) = (1/N(j))\sum_{i=0}^{N(j)} S(i)$$

where N(j) is the number of axial scans in the $j^{th}$ quadrant. Experience has shown that variability in values arising from single axial scans is too large to be useful, whereas quadrant averages, or the total average, are more meaningful. In accordance with a preferred version of the second embodiment of the present invention, the quadrants are chosen asymmetrically, i.e., they have different angular sizes, and are oriented to correspond with the asymmetric distribution of the nerve fibers as they cross the circular scan path on their way to the optic nerve head. The use of asymmetric quadrants is a significant improvement over the use of symmetric quadrants with boundaries oriented in the vertical and horizontal directions. Since glaucomatous NFL loss occurs preferentially along certain directions, it is believed that orienting the quadrants to correspond with the actual distribution will provide greater sensitivity to NFL loss. Glaucomatous NFL loss occurs preferentially in the two arcuate bundle regions, where the NFL is normally the thickest. The arcuate bundles exit the optic disc superiorly and inferiorly, then begins to turn in the temporal direction. Thus, it is advantageous to orient the superior and inferior quadrants slightly temporally to match the position of the arcuate bundles. It is well known to those of ordinary skill in the art how to determine the actual distribution.

The next step of the second embodiment of the present invention is to convert the quadrant averages and total average to logarithmic form (dB):

$$A^{log} = 10 \log_{10}(A)$$

The next step is to determine an NSR signal ratio for each quadrant j:

$$NSR(j) = A_{nfl}^{log}(j) - A_{Ref}^{log}(j)$$

Since it is expected that the NFL signal should increase with higher nerve fiber density and backscattering cross-sectional area, and the reference RPE+choriocapillaris signal should decrease with shadowing from a thicker NFL, in accordance with the second embodiment of the present invention, it is believed that the ratio NSR is a composite measure of NFL thickness, density, and scattering properties. In accordance with the second embodiment of the present invention, NSR is a measure that can be used to diagnose and monitor glaucomatous eyes and, as a result, can be used to discriminate between normal and glaucomatous eyes.

Figure 4:
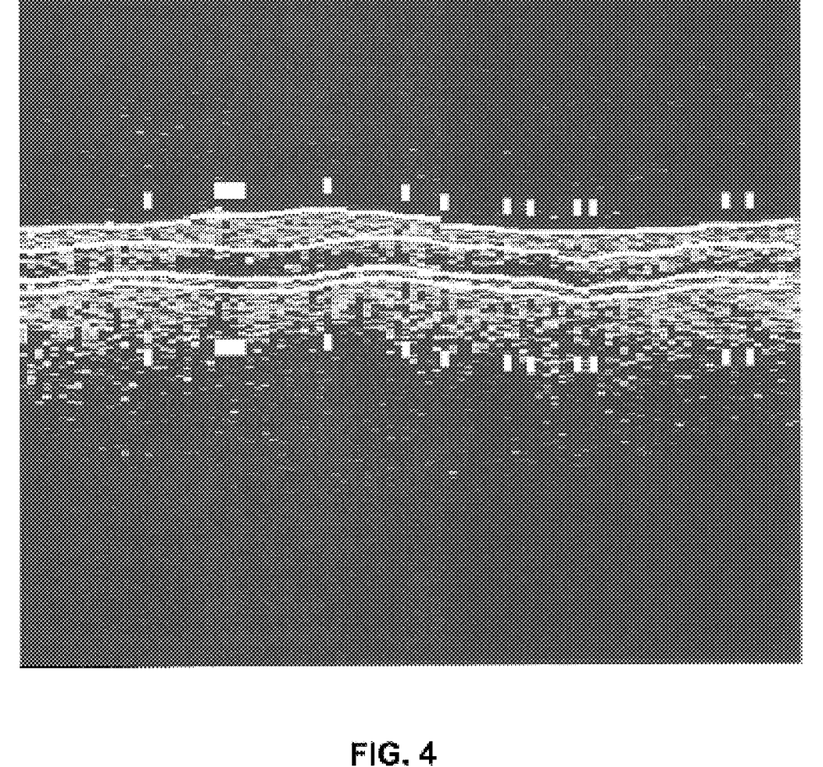
FIG. 4 shows scan data indicating retinal nerve fiber layer ("NFL") window and reference window and shadowed areas used to fabricate the second embodiment of the present invention.

FIG. 4 shows OCT data from a representative scan. Superimposed on the data are boundary lines showing the NFL window and the reference window. The white tic marks indicate regions having abnormally low signal strength (shadowing) in the reference window.

To test the efficacy of using NSR to discriminate between normal and glaucomatous eyes, a sample of each was scanned with OCT apparatus 1000. In accordance with the scan protocol, following dilation with tropicamide 1% and phenylephrine 2.5% topical drops, each eye was scanned, centered on the optic disc border, while the patient fixated on a target presented to the scanned eye. The scan data were processed using the above-described method, and the NSR total average was computed. It was found that the mean value for two populations (one population of normal subjects and one population of glaucomatous subjects) differed by approximately 10 times the measurement standard deviation for the normal population. Assuming a normal distribution, it is expected that the inventive method described herein can be used to detect NFL loss that is less than one-fourth as severe as early glaucomatous eyes in the study with 99% specificity.

Those skilled in the art will recognize that the foregoing description has been presented for the sake of illustration and description only. As such, it is not intended to be exhaustive or to limit the invention to the precise form disclosed.

What is claimed is:

1. A method for providing one or more measures for diagnosing and monitoring eye disease, which method comprises the steps of:

OCT scanning a retina of an eye to obtain an OCT scan image;

aligning axial scans in the OCT scan image;

for each axial scan in the OCT scan image:
 (a) locating a vitreo-retinal interface ("VRI") and a retina-pigment epithelium ("RPE") interface;
 (b) determining a threshold as a function of signal statistics in the axial scan;
 (c) determining a thickness of the NFL by counting pixels between the VRI and RPE interfaces that exceed the threshold; and averaging the thickness of the NFL over predetermined axial scans to provide the one or more measures.

2. The method of claim 1 wherein the step of aligning uses cross-correlation of axial scan waveforms.

3. The method of claim 1 wherein the step of locating the VRI and RPE interfaces comprises searching for a transition of signal strength across a threshold which is a predetermined amount below a maximum retinal signal.

4. The method of claim 3 wherein the maximum retinal signal is determined as an average of maximum retinal signals over a predetermined number of neighboring axial scans.

5. The method of claim 1 wherein the step of determining a threshold comprises determining a threshold as a function of an average signal in a predetermined portion of the axial scan below the RPE interface and a retinal signal.

6. The method of claim 5 wherein the retinal signal in the step of determining a threshold comprises a maximum retinal signal.

7. The method of claim 1 wherein the step of averaging the thickness of the NFL comprises detecting shadowing by blood vessels and eliminating or replacing an axial scan if shadowing by blood vessels is detected.

8. The method of claim 7 wherein the step of detecting shadowing comprises comparing a sum of signals in a predetermined portion of the axial scan below the RPE interface with the sum for a predetermined number of neighboring axial scans.

9. The method of claim 1 wherein the step of averaging the thickness of the NFL comprises averaging the NFL thickness over one or more of: a superior quadrant, an inferior quadrant, a nasal quadrant, a temporal quadrant, and an entire scan.

10. The method of claim 9 which further comprises the step of determining a ratio of a sum of the NFL thickness over the superior and inferior quadrants and a sum of the NFL thickness over the nasal and temporal quadrants.

11. A method for providing a measure for diagnosing and monitoring eye disease, which method comprises the steps of:

OCT scanning a retina of an eye to obtain an OCT scan image;

aligning axial scans in the OCT scan image;

for each axial scan in the OCT scan image:
(a) locating a vitreo-retinal interface ("VRI") and a retina-pigment epithelium ("RPE") interface;
(b) for a predetermined portion of the axial scan below the RPE interface ("reference window"), summing the signal strengths; and
(c) for a predetermined portion of the axial scan below the VRI interface ("NFL window"), summing the signal strengths;

averaging a representation of the sum of signal strengths in the reference window over predetermined axial scans;

averaging a representation of the sum of signals strengths in the NFL window over predetermined axial scans; and determining a ratio of the averages to form the measure.

12. The method of claim 11 wherein the step of aligning uses cross-correlation of axial scan waveforms.

13. The method of claim 11 wherein the NFL window has an inner border at the VRI and an outer border a fixed distance from the RPE.

14. The method of claim 11 wherein the step of locating the VRI and RPE interfaces comprises convolving axial scan data with an edge-detecting kernel.

15. The method of claim 11 wherein the step of summing the signal strengths in the reference window comprises summing in a linear signal domain.

16. The method of claim 11 which further comprises the step of detecting shadowing by blood vessels, and, if shadowing is detected, replacing a signal in shadowed axial scans with that from a neighboring axial scan or an average axial scan.

17. The method of claim 16 wherein the step of detecting shadowing by blood vessels comprises comparing the sum of signals in the reference window with the sum for a predetermined number of neighboring axial scans.

18. The method of claim 11 wherein the step of averaging a representation of the sum of signal strengths in the reference window and the NFL window comprises one or more of averaging the sum of signal strengths over quadrants and averaging over an entire OCT scan.

19. The method of claim 18 wherein the step of determining a ratio comprises:

converting the averages to a logarithmic form;

for each quadrant of the asymmetric distribution, subtracting the logarithmic forms of the sums in the NFL window and the reference window.

20. The method of claim 11 wherein step of averaging a representation of the sum of signal strengths in the reference window and the NFL window comprises averaging the sum of signal strengths over quadrants where the superior and inferior quadrants are slightly temporally oriented to match the positions of arcuate nerve fiber bundles crossing the OCT scan.

* * * * *